United States Patent
Holgate et al.

(10) Patent No.: US 10,307,271 B2
(45) Date of Patent: Jun. 4, 2019

(54) CONTROL SYSTEM AND METHOD FOR NON-GAIT ANKLE AND FOOT MOTION IN HUMAN ASSISTANCE DEVICE

(71) Applicant: Össur Iceland ehf, Reykjavik (IS)

(72) Inventors: Matthew A. Holgate, Chandler, AZ (US); Chase Wheeler, Mesa, AZ (US)

(73) Assignee: Össur Iceland ehf, Reykjavik (IS)

( * ) Notice: Subject to any disclaimer, the term of this patent is extended or adjusted under 35 U.S.C. 154(b) by 0 days.

(21) Appl. No.: 15/341,817

(22) Filed: Nov. 2, 2016

(65) Prior Publication Data
US 2017/0071762 A1 Mar. 16, 2017

Related U.S. Application Data

(63) Continuation-in-part of application No. 14/210,331, filed on Mar. 13, 2014, now Pat. No. 9,622,884, (Continued)

(51) Int. Cl.
*A61F 2/70* (2006.01)
*A61F 2/68* (2006.01)
(Continued)

(52) U.S. Cl.
CPC .......... *A61F 2/68* (2013.01); *A61F 2/60* (2013.01); *A61F 2/66* (2013.01); *A61F 2/76* (2013.01);
(Continued)

(58) Field of Classification Search
CPC .................................................. A61F 2/72
See application file for complete search history.

(56) References Cited

U.S. PATENT DOCUMENTS 5,430,643 A * 7/1995 Seraji .................. B25J 9/1643
318/568.11
7,112,938 B2   9/2006 Takenaka et al.
(Continued)

FOREIGN PATENT DOCUMENTS

WO   2006076164 A2   7/2006
WO   2011005482 A2   1/2011
(Continued)

OTHER PUBLICATIONS

Au S. et al., "Biomechanical Design of a Powered Ankle-Foot Prosthesis," in Rehabilitation Robotics, 2007. ICORR 2007. IEEE 10th International Conference on, 2007, pp. 298-303.
(Continued)

*Primary Examiner* — Jacqueline Wozincki
(74) *Attorney, Agent, or Firm* — Knobbe, Martens, Olson & Bear, LLP

(57) ABSTRACT

A human assistance device has a rate gyro, first accelerometer, and second accelerometer disposed on a mobile body for sensing a physical state of the mobile body to provide a physical state measurement. The human assistance device can be a prosthetic, orthotic, and robotic device. An ATAN2 function is performed on an output of the first accelerometer and an output of the second accelerometer. An output of the rate gyro and an output of the ATAN2 function is filtered to provide a filtered physical state measurement. The filtered physical state measurement is applied to a reference function to generate a reference command to control a non-gait motion of an actuator in the human assistance device. The reference command controls the human assistance device, for example to provide a shifting foot position while seated, with a natural, biological motion, without an artificial or mechanical appearance.

21 Claims, 8 Drawing Sheets

Related U.S. Application Data which is a continuation-in-part of application No. 13/767,945, filed on Feb. 15, 2013.

(60) Provisional application No. 61/600,141, filed on Feb. 17, 2012, provisional application No. 61/790,259, filed on Mar. 15, 2013.

(51) Int. Cl.
    *A61F 2/76* (2006.01)
    *A61F 5/02* (2006.01)
    *A61F 2/66* (2006.01)
    *A61F 2/60* (2006.01)
    *A61F 2/72* (2006.01)

(52) U.S. Cl.
    CPC ....... *A61F 5/02* (2013.01); *A61F 2/72* (2013.01); *A61F 2002/704* (2013.01); *A61F 2002/762* (2013.01); *A61F 2002/764* (2013.01); *A61F 2002/7625* (2013.01); *A61F 2002/7635* (2013.01); *A61F 2002/7645* (2013.01)

(56) References Cited

U.S. PATENT DOCUMENTS

| | | |
|---|---|---|
| 7,300,240 B2 | 11/2007 | Brogrardh |
| 7,431,737 B2 | 10/2008 | Ragnarsdottir et al. |
| 7,811,333 B2 | 10/2010 | Jonsson et al. |
| 7,896,927 B2 | 3/2011 | Clausen et al. |
| 8,057,550 B2 | 11/2011 | Clausen et al. |
| 8,287,477 B1 | 10/2012 | Herr et al. |
| 8,419,804 B2 | 4/2013 | Herr et al. |
| 8,551,184 B1 | 10/2013 | Herr |
| 8,601,897 B2 | 12/2013 | Lauzier |
| 8,716,877 B2 | 5/2014 | Sugar et al. |
| 8,734,528 B2 | 5/2014 | Herr et al. |
| 9,459,698 B2 * | 10/2016 | Lee .................. G06F 3/017 |
| 2002/0007690 A1 | 1/2002 | Song et al. |
| 2005/0070834 A1 | 3/2005 | Herr et al. |
| 2006/0025959 A1 | 2/2006 | Gomez et al. |
| 2006/0046907 A1 | 3/2006 | Rastegar et al. |
| 2006/0122710 A1* | 6/2006 | Bedard ................. A61F 2/644 623/24 |
| 2006/0135883 A1 | 6/2006 | Jonsson et al. |
| 2006/0173552 A1 | 8/2006 | Roy |
| 2006/0189899 A1 | 8/2006 | Flaherty et al. |
| 2007/0129653 A1 | 6/2007 | Sugar et al. |
| 2008/0058668 A1 | 3/2008 | Seyed Momen et al. |
| 2009/0088912 A1 | 4/2009 | Rajaraman |
| 2010/0161077 A1 | 6/2010 | Boone et al. |
| 2010/0275718 A1 | 11/2010 | Stuart et al. |
| 2011/0126660 A1 | 6/2011 | Lauzier et al. |
| 2011/0132131 A1 | 6/2011 | Worz |
| 2011/0224804 A1 | 9/2011 | Clausen et al. |
| 2012/0078415 A1 | 3/2012 | Kubo et al. |
| 2012/0153875 A1 | 6/2012 | Glaister |
| 2012/0226364 A1* | 9/2012 | Kampas ................ A61F 2/64 623/24 |
| 2014/0114437 A1 | 4/2014 | Herr et al. |
| 2014/0121782 A1 | 5/2014 | Herr et al. |
| 2015/0127118 A1 | 5/2015 | Herr et al. |
| 2015/0223952 A1 | 8/2015 | Langlois et al. |

FOREIGN PATENT DOCUMENTS

| | | |
|---|---|---|
| WO | 2011096965 A2 | 8/2011 |
| WO | 2013086035 A1 | 6/2013 |

OTHER PUBLICATIONS

Au S. et al., "Powered Ankle—Foot Prosthesis Improves Walking Metabolic Economy," Robotics, IEEE Transactions on, vol. 25, pp. 51-66, 2009.

Au S. et al., "Powered Ankle-Foot Prosthesis for the Improvement of Amputee Ambulation," in Engineering in Medicine and Biology Society, 2007. EMBS 2007. 29th Annual International Conference of the IEEE, 2007, p. 3020.

Au S. et al. "Powered ankle-foot prosthesis to assist level-ground and stair-descent gaits," Neural Networks, 21, 2008, pp. 654-666.

Au S. et al, "Powered ankle-foot prosthesis," Robotics & Automation Magazine, IEEE, vol. 15, pp. 52-59, 2008.

Au S., "Powered Ankle-Foot Prosthesis for the Improvement of Amputee Walking Economy," Massachusetts Institute of Technology, 2007, pp. 1-108.

Belforte G. et. al., "Pneumatic Active Gait Orthosis". Mechatronics 11, 2001, pp. 301-323.

Bellman R. et al., "SPARKy 3: Design of an Active Robotic Ankle Prosthesis with two Actuated Degrees of Freedom Using Regenerative Kinetics", 2nd IEEE RAS & EMBS International Conference on Biomedical Robotics and Biomechatronics, pp. 511-516, 2008.

Bernardi, M. et al., (1995), "The Efficiency of Walking of Paraplegic Patients Using a Reciprocating Gait Orthosis," Spinal Cord 33(7): 409-415.

Boehler, Alexander W. et al., (2008), "Design, Implementation and Test Results of a Robust Control Algorithm for a Powered Ankle Foot Orthosis," IEEE International Conference on Robotics and Automation (ICRA), IEEE.

Colombo Gery et. al., "Treadmill Training of Paraplegic Patients Using a Robotic Orthosis", Journal of Rehabilitation Research and Development. vol. 37 No. 6., 2000, pp. 693-700.

Farley C. et al., "Biomechanics of Walking and Running: Center of Mass Movements to Muscle Action," Exerc Sport Sci Rev, vol. 26, pp. 253-285, 1998.

Guiraud D., "Application of an Artificial Neural Network to the Control of an Active External Orthosis of the Lower Limb", Medical & Biological Engineering & Computing, Nov. 1994, vol. 32, pp. 610-614.

Hansen A. et al., "The Effects of Prosthetic Foot Roll-over Shape Arc Length on the Gait of Trans-tibial Prosthesis Users," Prosthetics and Orthotics International, vol. 30, No. 3, 286-299, 2006.

Hansen A. et al., "The human ankle during walking: implications for design of biomimetic ankle prostheses and orthoses," Journal of Biomechanics, 37(10): 1467-1474, 2004.

Hansen A. et al., "Prosthetic ankle-foot mechanism capable of automatic adaptation to the walking surface," J Biomech Eng-T ASME, 131(3): 035002, 2009.

Herr H. et al., "Patient-Adaptive Prosthetic and Orthotic Leg Systems", Proceedings of the International Federation for Medical & Biological Engineering, Reykjavik, Iceland, Jun. 18-22, 2002, pp. 18-21.

Hitt J. et al., "A Robotic Transtibial Prosthesis with Regenerative Kinetics: The Design Analyses, Methods, and Testing", U.S. Army Military Amputee Research Program, 2008.

Hitt J. et al., "An Active Foot-Ankle Prosthesis with Biomechanical Energy Regeneration", Journal of Medical Devices,vol. 4, 2010.

Hitt, Joseph et al., (2010), "Bionic Running for Unilateral Transtibial Military Amputees," Proceedings of the 27th Army Science Conference, Orlando, FL.

Hitt, Joseph et al., (2010), "Dismounted Soldier Biomechanical Power Regeneration Kit (SPaRK)," Proceedings of the 27th Army Science Conference, Orlando, FL.

Hitt J. et al., "Robotic Transtibial Prosthesis with Biomechanical Energy Regeneration", Industrial Robot: An International Journal, vol. 36, Issue 5, pp. 441-447, 2009.

Hitt J. et al., "The SPARKy (Spring Ankle with Regenerative Kinetics) Project: Design and Analysis of a Robotic Transtibial Prosthesis with Regenerative Kinetics", ASME International Design Engineering Technical Conferences & Computers and Information in Engineering Conference (IDETC/CIE), CD-ROM, pp. 1-10, 2007.

Holgate M., "Control of a Robotic Transtibial Prosthesis", A Dissertation, Arizona State University, Dec. 2009.

Holgate M. et al., "A Control Algorithm for a Prosthetic Ankle Using Phase Plane Invariants", Poster presentation at Dynamic Walking, Vancouver, Canada, 2009.

(56) References Cited

OTHER PUBLICATIONS

Holgate M. et al., "A Novel Control Algorithm for Wearable Robotics Using Phase Plane Invariants", International Conference on Robotics and Automation, 2009.
Holgate M. et al., "Control Algorithms for Ankle Robots: A Reflection on the State-of-the-Art and Presentation of Two Novel Algorithms", 2nd IEEE RAS & EMBS International Conference on Biomedical Robotics and Biomechatronics, pp. 97-103, 2008.
Holgate M., "The SPARKy (Spring Ankle with Regenerative Kinetics) Project: Choosing a DC Motor Based Actuation Method" 2nd IEEE RAS & EMBS International Conference on Biomedical Robotics and Biomechatronics, pp. 163-168, 2008.
Hollander, Kevin W. et al., (2005), "A Robotic "Jack Spring" for Ankle Gait Assistance," DETC2005-84492, ASME International Design Engineering Technical Conference (IDETC2005), Long Beach, CA, American Society of Mechanical Engineers.
Hollander K. et al. "A Robust Control Concept for Robotic Ankle Gail Assistance," IEEE International Conference on Rehabilitation Robotics (ICORR), 2007, pp. 119-123.
Hollander, Kevin W. et al., (2006), "An Efficient Robotic Tendon for Gait Assistance," Journal of biomechanical engineering 128: 788.
Kawamoto, Hiroaki et al., (2003), "Power Assist Method for HAL-3 Estimating Operator's Intention Based on Motion Information," IEEE International Workshop on Robot and Human Interactive Communication, Millbrae, CA.
Kazerooni, H. et al., (2005), "On the Control of the Berkeley Lower Extremity Exoskeleton (BLEEX)," Proceedings of the 2005 IEEE International Conference on Robotics and Automation, Barcelona, Spain, Apr. 2005.
Kyriakopoulos K. et al., "Minimum jerk path generation." International Conference on Robotics and Automation, 1:364-369, 1988.
Norris, James A. et al., (2007), "Effect of Augmented Plantarflexion Power on Preferred Walking Speed and Economy in Young and Older Adults," Gait & Posture 25(4): 620-627.

Sawicki, Gregory S. et al., (2009), "It Pays to Have a Spring in your Step," Exercise and Sport Sciences Reviews 37(3).
Sawicki, Gregory S. et al., (2009), "Powered Ankle Exoskeletons Reveal the Metabolic Cost of Plantar Flexor Mechanical Work During Walking with Longer Steps at Constant Step Frequency," Journal of Experimental Biology 212(1).
Sawicki, Gregory S. et al., (2009), "Mechanics and Energetics of Incline Walking with Robotic Ankle Exoskeletons," Journal of Experimental Biology 212(1).
Sugar, Thomas G., (2002), "A Novel Selective Compliant Actuator," Mechatronics 12(9-10): 1157-1171.
Sup F. et al., "Design and control of an active electrical knee and ankle prosthesis," in Biomedical Robotics and Biomechatronics, 2008. BioRob 2008. 2nd IEEE RAS & EMBS International Conference on, 2008, pp. 523-528.
Walsh, Conor James et al., (2006), Biomimetic Design of an Under-Actuated Leg Exoskeleton for Load-Carrying Augmentation, Cambridge, MA, Massachusetts Inst of Tech, M.S.
Walsh, Conor James et al., "Development of a Lightweight, Under-Actuated Exoskeleton for Load-Carrying Augmentation," Proceedings of the 2006 IEEE International Conference on Robotics and Automation, Orlando, Florida, May 2006.
Ward, Jeffrey et al., (2008), "Control Architectures for a Powered Ankle Foot Orthsosis," International Journal of Assistive Robotics and Mechatronics 9(2): 2-13.
Ward, Jeffrey et al., (2007), "Robotic Gait Trainer Reliability and Stroke Patient Case Study," IEEE 10th International Conference on Rehabilitation Robotics (ICORR), Holland.
Ward, Jeffrey et al., (2010), "Stroke Survivor Gait Adaptation and Performance After Training on a Powered Ankle Foot Orthosis," Proceedings of the IEEE International Conference on Robotics and Automation (ICRA), Anchorage, AK, IEEE.
Ward Jeffrey et al., (2011), "Using the Translational Potential Energy of Springs for Prosthetic Systems," IEEE Multi-conference on Systems and Control, Denver, CO, IEEE.

* cited by examiner

CONTROL SYSTEM AND METHOD FOR NON-GAIT ANKLE AND FOOT MOTION IN HUMAN ASSISTANCE DEVICE

CLAIM TO DOMESTIC PRIORITY

The present application is a continuation-in-part of U.S. patent application Ser. No. 14/210,331, filed Mar. 13, 2014, which is a continuation-in-part of U.S. patent application Ser. No. 13/767,945, filed Feb. 15, 2013, which claims the benefit of U.S. Provisional Application No. 61/600,141, filed Feb. 17, 2012, which applications are incorporated herein by reference. U.S. patent application Ser. No. 14/210,331 further claims the benefit of U.S. Provisional Application No. 61/790,259, filed Mar. 15, 2013, which application is incorporated herein by reference.

FIELD OF THE INVENTION

The present invention relates in general to a human assistance device, and more particularly, to a control system and method for non-gait ankle and foot motion in the human assistance device.

BACKGROUND OF THE INVENTION

Prosthetic and orthotic devices help restore mobility to people who lack able-bodied motion. Prosthetic devices are intended to replace the appearance of a missing limb or portion of a limb and can return mobility to the wearer or user. Orthotic devices are intended to support or supplement an existing limb, by assisting with movement, reducing weight-bearing loads on the body, reducing pain, and increasing endurance. Prosthetic and orthotic devices are available to replace or support various portions of the body. Lower limb prosthetic devices include a prosthetic foot, foot-ankle prosthesis, prosthetic knee joint, and prosthetic hip joint. Lower limb orthotic devices include a foot orthoses, ankle-foot orthoses, knee-ankle-foot orthoses, and knee orthoses. People who require a lower limb prosthesis or orthosis often expend more metabolic power to walk or move at the same speed as able-bodied individuals.

Human locomotion, such as walking and running, is commonly described in terms of gait. Gait is a cyclical pattern of leg and foot movement that creates locomotion. A gait cycle is defined for a single leg and begins with the initial contact of the foot with the ground or heel strike. The conclusion of a gait cycle occurs when the same foot makes a second heel strike. The gait cycle can be divided into two phases, stance phase and swing phase. Stance phase begins with heel strike and ends when the toe of the same foot leaves the ground. Swing phase begins when the foot leaves contact with the ground and ends with the heel strike of the same foot. One goal of lower limb prosthetic and orthotic devices is to help the user achieve a normal gait, while reducing energy expended by the user.

Most if not all control systems for prosthetic and orthotic devices have focused on gait and other cyclical patterns of motion. Yet, humans spend a considerable portion of the day involved in non-gait activities, while wearing the prosthetic or orthotic device. For example, the person may slide foot position or cross legs while sitting in a chair, or change balance point while leaning against a bar or podium, or shift stance while standing in a social gathering. The person may be engaged in random, complex, non-cyclic activities, such as dancing, exercise routines, or sporting activities, while wearing the prosthetic or orthotic device. The person may be wearing long pants or long dress that covers the prosthetic or orthotic device. In any case, the person likely prefers the non-gait activity while wearing the prosthetic or orthotic device to appear as natural as possible, without indicating, revealing, or otherwise drawing attention to the presence of the prosthetic or orthotic device. The non-gait activity should appear as biological motion, without an artificial or mechanical appearance.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, those skilled in the art will appreciate that the description is intended to cover alternatives, modifications, and equivalents as may be included within the spirit and scope of the invention as defined by the appended claims and their equivalents as supported by the following disclosure and drawings.

Figure 1:
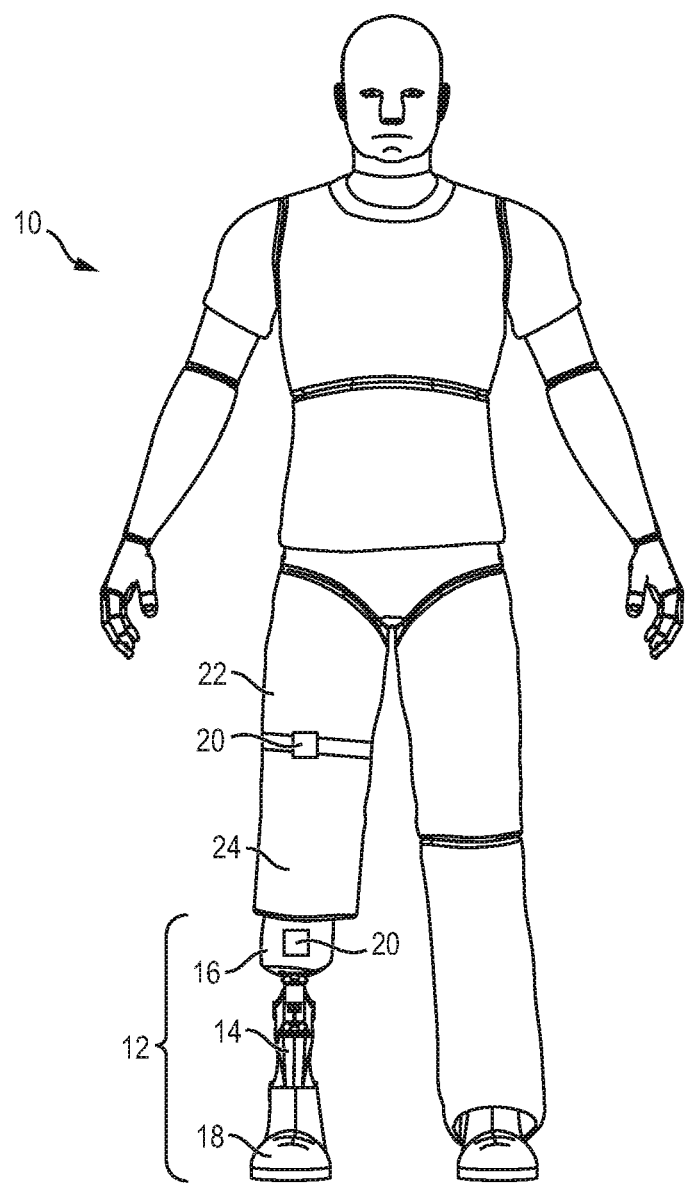
FIG. 1 illustrates a user wearing an active lower limb prosthesis.

FIG. 1 shows an example of user 10 wearing an active lower limb prosthesis 12, which includes a control system for controlling the operation of the prosthesis. Lower limb prosthesis 12 is an active prosthetic device or wearable robotic device, including active and passive components. In one embodiment, lower limb prosthesis 12 is a below-the-knee prosthesis, also known as a foot-ankle prosthesis. In another embodiment, lower limb prosthesis 12 includes a robotic or prosthetic joint, such as an ankle joint or knee joint.

Lower limb prosthesis 12 includes an ankle prosthesis 14, shank portion 16, and foot portion 18. Ankle prosthesis 14 includes active components, such as one or more actuators, controlled by a computer system or microcontroller with local electronic memory. A sensor or sensor system 20 is worn by user 10. In one embodiment, sensor 20 is worn on thigh 22, tibia 24, or other part of user 10. In another embodiment, sensor 20 is disposed on ankle prosthesis 14, shank portion 16, or foot portion 18. In yet another embodiment, a plurality of sensors 20 is disposed on user 10 and/or lower limb prosthesis 12. Sensor 20 detects a kinematic state, loading state, or kinematic state and loading state of user 10. Measurements from sensor 20 are used by the control system to control ankle prosthesis 14 and lower limb prosthesis 12.

Figure 2:
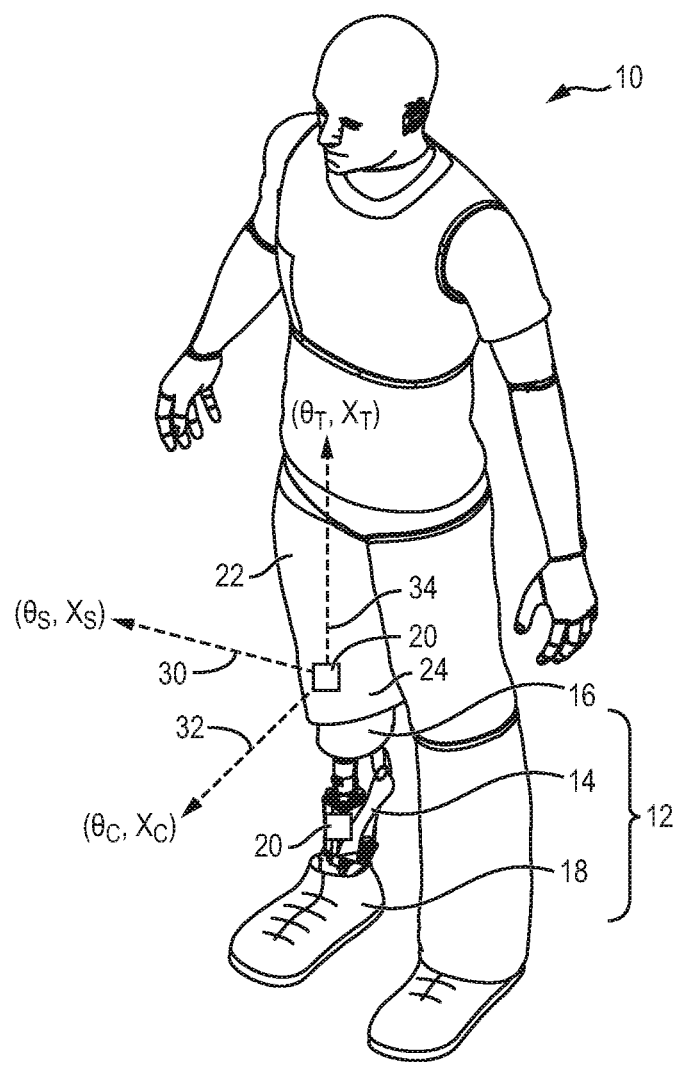
FIG. 2 illustrates a coordinate system for measuring motion in the active lower limb prosthesis.

FIG. 2 shows a coordinate system for measuring non-gait activities involving ankle prosthesis 14 and lower limb prosthesis 12. Sensor 20 measures a kinematic state or loading state of a mobile body of user 10. A mobile body includes a limb segment or robotic segment. In one embodiment, the mobile body is ankle prosthesis 14, shank portion 16, foot portion 18, or tibia 24. A kinematic state includes an angular position, linear position, linear velocity, angular velocity, linear acceleration, or angular acceleration with an associated frame of reference to the mobile body. A loading state includes a moment or force on the mobile body.

Sensors 20 are configured to measure kinematic state, such as velocities, accelerations, angular positions, and linear positions in coordinate frames, as oriented with the limb segment or robotic segment. A limb segment includes thigh 22 or tibia 24 of user 10. A robotic segment includes ankle prosthesis 14, shank portion 16, or foot portion 18 of lower limb prosthesis 12. Sensor 20 determines the kinematic state of user 10 in linear coordinates, polar coordinates, or a combination of coordinate systems. The coordinate frames have three orthogonal axes: a sagittal axis ($\theta_s$, $X_s$), coronal axis ($\theta_c$, $X_c$), and transverse axis ($\theta_T$, $X_T$). The sagittal direction 30 is in the direction of sagittal axis ($\theta_s$, $X_s$) normal to the sagittal plane of the mobile body. The coronal direction 32 is in the direction of coronal axis ($\theta_c$, $X_c$) normal to the coronal plane of the mobile body. The transverse direction 34 is in the direction of transverse axis ($\theta_T$, $X_T$) normal to the transverse plane of the mobile body. Each sensor 20 is oriented so that the axis of measurement can be expressed as a linear combination of three unit vectors in the direction of the sagittal axis ($\theta_s$, $X_s$), coronal axis ($\theta_c$, $X_c$), and transverse axis ($\theta_T$, $X_T$).

Figure 3:
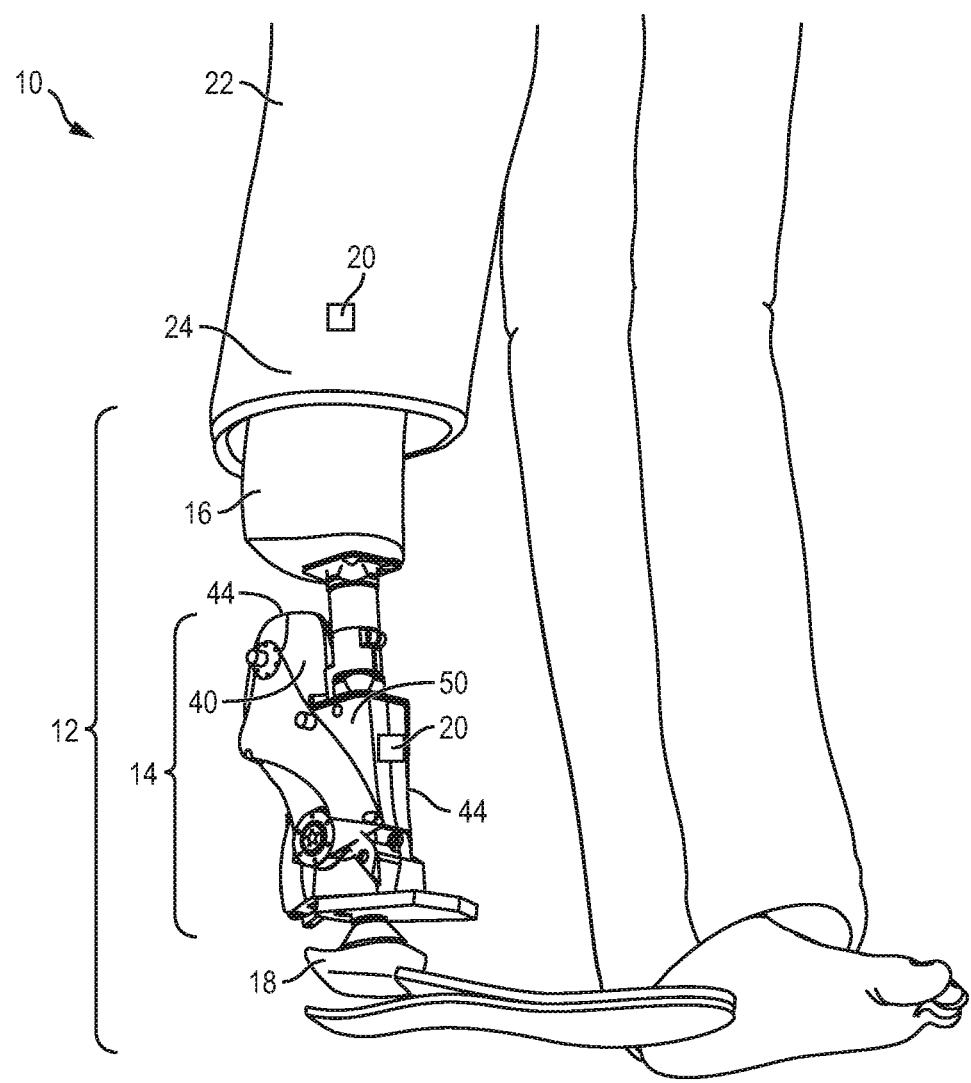
FIG. 3 illustrates further detail of the active lower limb prosthesis.

FIG. 3 shows further detail of lower limb prosthesis 12, including ankle prosthesis 14, shank portion 16, and foot portion 18. Shank portion 16 of lower limb prosthesis 12 includes a socket or couples to a socket, which fits onto a residual limb of user 10, such as tibia 24. Ankle prosthesis 14 is coupled to shank portion 16, and foot portion 18 is coupled to ankle prosthesis 14. Ankle prosthesis 14 includes one or more active members or actuators 40, such as a motor, and may include one or more compliant members, such as a spring or beam, disposed within housing 44 of ankle prosthesis 14. A control system or controller 50 is disposed within housing 44 of ankle prosthesis 14 and coupled to actuator 40. Control system 50 responds to an input from sensor 20 and outputs a reference command to control actuator 40 in non-gait movement of ankle prosthesis 14.

Figure 4:
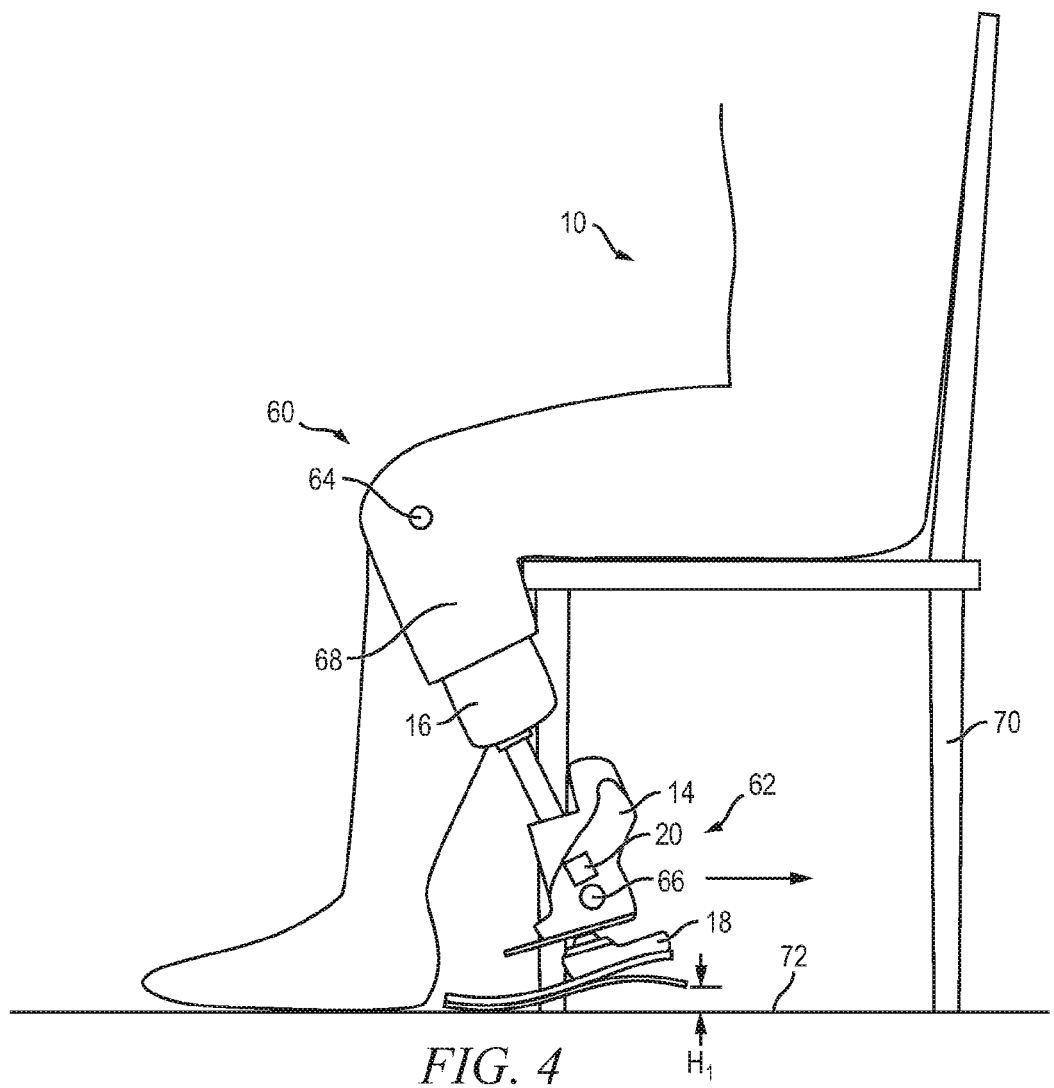
FIG. 4 illustrates a non-gait activity of shifting foot position with the active lower limb prosthesis.

FIG. 4 shows user 10 in the seated position on chair or bench 70 with a shifting motion of lower limb prosthesis 12 in a backward direction under the chair with the heel of foot portion 18 rises from the floor by height Hi, while the ball of foot portion 18 remains in contact with ground or floor 72. The motion lower limb prosthesis 12 in FIG. 4 is an exemplary non-gait activity and should be a natural, biological motion, without an artificial or mechanical appearance. To measure and control the non-gait foot shifting motion, sensor 20 includes an accelerometer, rate gyro, potentiometer, inclinometer, or other sensor to measure velocity, acceleration, angular position, linear position, or a combination thereof. In one embodiment, sensor 20 determines velocity, acceleration, angular position, or linear position of ankle prosthesis 14 with respect to the sagittal axis ($\theta_s$, $X_s$), coronal axis ($\theta_c$, $X_c$), and transverse axis ($\theta_T$, $X_T$). The kinematic state measurements from sensors 20 are used as inputs for control system 50. Measurements from sensors 20 are ultimately used to control an actuator of ankle prosthesis 14, lower limb prosthesis 12, or other wearable robotic device.

Figure 5:
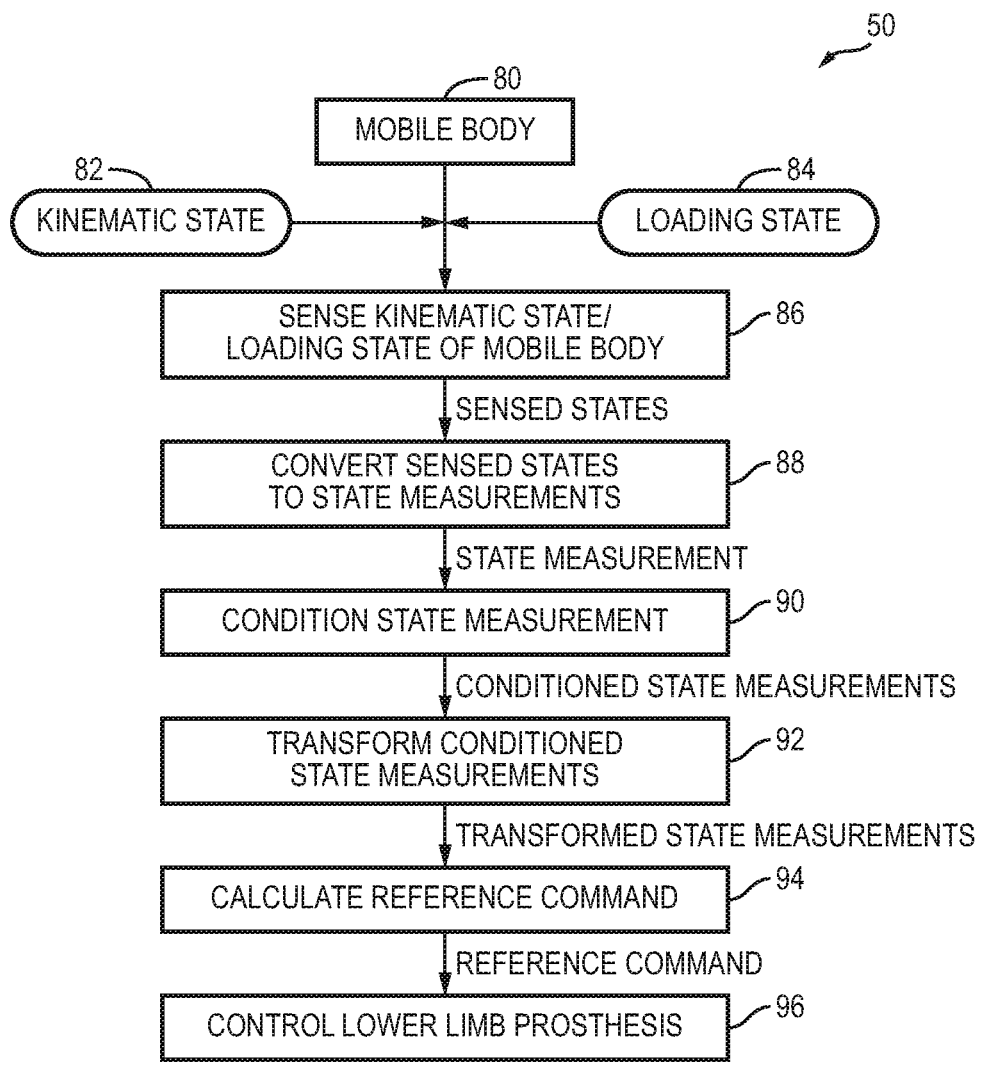
FIG. 5 illustrates a block diagram of a control system for controlling non-gait activity with a human assistance device.

FIG. 5 shows a block diagram of a method for controlling non-gait activities with a human assistance device using control system 50. Control system 50 includes a computer system or microcontroller with local electronic memory to store and process data from sensor 20 and generate a reference command output signal to control actuator 40. The method for controlling non-gait activity for lower limb prosthetic 12, or other prosthetic, orthotic, and robotic devices, collectively referred to as a human assistance device, and includes a series of operations performed on kinematic or loading data. The operations performed by control system 50 relate kinematic motion to a requisite output of actuator 40 or other control function of lower limb prosthetic 12.

The method for controlling non-gait activity for lower limb prosthetic 12, or other prosthetic, orthotic, and robotic devices, using control system 50 involves one or more mobile bodies 80 under a physical condition of one or more kinematic states 82, loading states 84, or combination of kinematic states 82 and loading states 84. Sensing block 86 detects or measures kinematic states 82 and/or loading states 84 of mobile body 80. In particular, sensor 20 detects or measures one or more kinematic states 82, loading states 84, or combination of kinematic states 82 and loading states 84 of one or more mobile bodies 80. Kinematic state 82 and loading state 84 comprise physical states of mobile body 80. The output of sensing block 86 is a sensed state measurement representing kinematic states 82 and loading states 84 sensed by sensor 20.

In conversion block 88, the sensed state measurement is converted in control system 50 to a unit of measurement compatible with reference command block 94. Conversion block 88 converts the sensor output, e.g. voltage or digital measurement, to a coordinate system compatible with reference command block 94, e.g. radians, radians per second, or G-force. The output of conversion block 88 is the physical state measurement.

In conditioning block 90, the state measurements are conditioned in control system 50 by various numeric processing operations, such as Kalman filtering, transfer function, integration, differentiation, and amplification. Conditioning block 90 can use any combination and order of the conditioning operations on the state measurements and repeated as necessary. In one embodiment, conditioning block 90 includes amplification, attenuation, or gain of any nonzero number, including unity gain, of the state measurements. Filtering is employed for multiple uses including noise reduction in the state measurements. For example, conditioning block 90 may implement a low pass filter. Other conditioning operations can use interpolation and substitution to reduce inaccuracies in the state measurements, and adjustment and alteration of the state measurements. Alteration of the state measurements is performed in a manner similar to integration or differentiation to reduce drift in numerical integration or noise in numerical differentiation. The output of conditioning block 90 is the conditioned state measurements.

In transformation block 92, the conditioned state measurements are transformed in control system 50 to change coordinate system using isometric or non-isometric transformations. The types of transformations for changing coordinate systems include rotations and dilations. Other types of transformations include identity transformations, orthogonal projections, oblique projections, changes to other coordinate systems, and changes of scale. In addition, other coordinate systems include polar coordinate systems, barycentric coordinate systems, and similar types of coordinate systems. Changes of scale include log scale or any other function of scale. Moreover, the transformations may include any transformation as a mathematical function of the conditioned state measurements, or any combination in any order of transformations, projections, changes of coordinate system, changes of scale, or other mathematical function. The output of transformation block 92 is the transformed state measurements.

The transformed state measurement coordinate system may have the same number or a different number of dimensions as the conditioned state measurement coordinate system. In fact, there may be more or less transformed state measurements than conditioned state measurements. In one embodiment, transformation block 92 transforms state measurements to time independent data for the reference function, e.g. creating phase plane, and surfaces defining possible positions of angular velocity. In another embodiment, transformation block 92 convert time dependent measurements, e.g. angular velocity over time, to time independent measurements, a non-temporal based phase angle and polar radius in a phase plot or polar plot.

In an alternative embodiment, transforming block 92 is performed prior to conditioning block 90. In this case, the state measurements are transformed in transformation block 92 of control system 50 to yield the transformed state measurements. The transformed state measurements are conditioned in conditioning bock 90 of control system 50 to yield the conditioned state measurements. In either embodiment, conditioning block 90 prior to transformation block 92, or transformation block 92 prior to conditioning block 90, the result is conditioned and transformed state measurements.

In calculate reference command block 94, the transformed state measurements (or conditioned state measurements) are used as arguments in one or more reference command functions to calculate reference commands. The reference function is represented with a function that accepts inputs and that outputs a unique value for each combination of inputs. The reference function includes look up tables, mathematical functions, or combinations of tables and mathematical functions, or other suitable method stored in the electronic memory and executed by the computer system or microprocessor.

In one embodiment, the reference function is determined by recording data from similar non-gait activities in an able-bodied individual. One or more sensors, similar to sensors 20, are coupled to an able-bodied test subject to detect physical states, such as kinematic or loading states, of biological activities. For example, the able-bodied test subject sits in a chair, similar to FIG. 4, and shifts position of his/her foot in a backward direction under the chair while remaining contact with the ground. The sensors on the able-bodied test subject monitor kinematic states and loading states, as well as sagittal axis, coronal axis, and transverse axis of motion, of the biological non-gait activity associated with shifting the foot in continuous contact with the ground while sitting. After sensing the physical states of the able-bodied test subject, the non-gait data is processed and used for the reference function. Able-bodied non-gait data can be processed using a series of operations, such as conversion block 88, conditioning block 90, and transformation block 92 to produce the reference function of natural, biological non-gait activity. The reference function is produced to match data from one or more non-gait activities, such as shifting position of lower limb prosthesis 12 while sitting, standing, or leaning. Other non-gait activities include random, complex, non-cyclic motions, such as dancing, exercise routines, sporting activities, or other similar activities. In another embodiment, the transformed state measurements are combined with a recording or a calculation of a desired reference command to achieve a natural, biological motion, without an artificial or mechanical appearance. The output of calculate reference command block 94 is the reference command.

In control block 96, the reference command produced by reference command block 94 controls operation of lower limb prosthesis 12, e.g. motion of actuator 40. Control system 50 is a continuous function relating the operation of lower limb prosthesis 12 to a measured signal. The continuous nature of control system 50 eliminates decision making by the system, if-then logic, and changes in state. An invariant signal, such as tibia angle, is used to control the non-gait activity for the prosthetic, orthotic, or robotic device. By measuring kinematic or leading states, control system 50 adapts to changes in the non-gait activity. Control system 50 continuously calculates an output, rather than waiting on a non-gait event to trigger an output. The measured signal is phase locked to the user's non-gait motion, and thus, the output of control system 50 is phase locked to the user's non-gait motion rather than being time based. Because control system 50 is not time-based, control system 50 better adapts to changes in non-gait activity.

Figure 6:
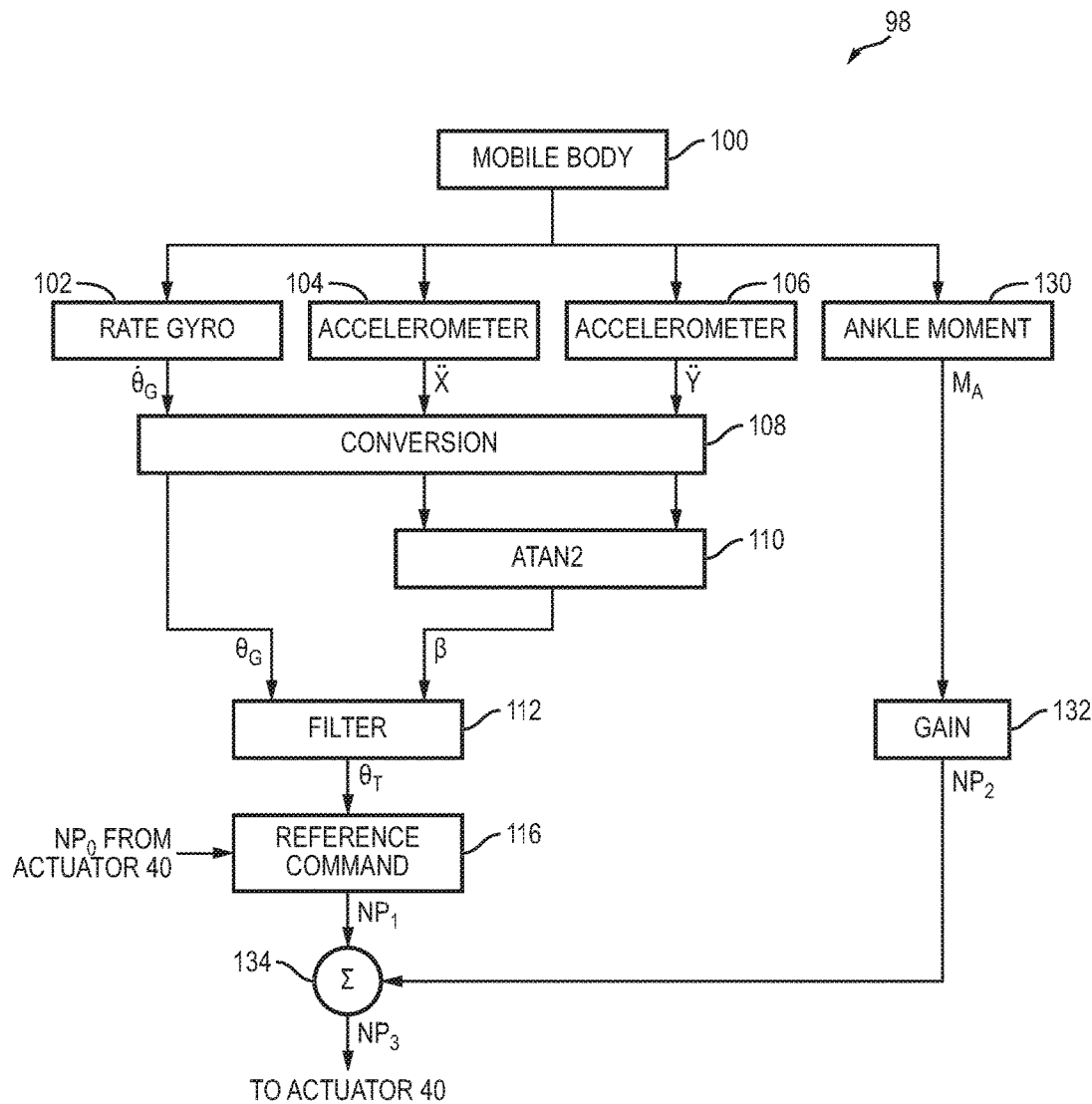
FIG. 6 illustrates a block diagram of a control system for controlling a non-gait activity of a lower limb prosthesis.

FIG. 6 shows a block diagram showing a control system 98 implemented in a computer system or microcontroller with local electronic memory to control non-gait activities of ankle prosthesis 14. In particular, control system 98 controls foot positioning of ankle prosthesis 14. A plurality of sensors, e.g. rate gyro and accelerometers, is disposed on mobile body 100, e.g. residual tibia 68 of user 10 or ankle prosthesis 14, to measure velocity, acceleration, angular position, or linear position with respect to the sagittal axis ($\theta_s$, $X_s$), coronal axis ($\theta_c$, $X_c$), and transverse axis ($\theta_T$, $X_T$). Rate gyro 102 measures an angular velocity $\theta_s$ as a kinematic state of residual tibia 68 of user 10 or ankle prosthesis 14 in sagittal direction 30.

Accelerometer 102 measures acceleration $\ddot{X}$ as a kinematic state of residual tibia 68 of user 10 or ankle prosthesis 14 in coronal direction 32. Accelerometer 104 measures acceleration $\ddot{Y}$ as a kinematic state of ankle prosthesis 14 in transverse direction 34. Acceleration $\ddot{X}$ and acceleration $\ddot{Y}$ represent 2D acceleration of residual tibia 68 of user 10 or ankle prosthesis 14.

Rate gyro 102, accelerometers 104 and 106, and ankle moment 130 correspond to sensing block 86 providing the sensed states in FIG. 5. The sensed states are converted to a unit of measurement compatible with reference command block 116. Conversion block 108 converts the sensor outputs of rate gyro 102 and accelerometers 106 and 108 to a coordinate system compatible with reference command block 116, e.g. digital measurement to radians or radians per second.

The acceleration $\ddot{X}$ and acceleration $\ddot{Y}$ are input arguments to ATAN2 block 110. ATAN2 block 110 implements an arctangent function with two arguments and determines angle and magnitude. ATAN2 block 110 is implemented in the computer system or microcontroller with local electronic memory and determines the appropriate quadrant of the angle in radians between π and −π based on the signs of the input arguments. ATAN2 block 100 provides output angle β in response to acceleration $\ddot{Y}$ and acceleration $\ddot{Y}$. Conversion block 108 may convert the output angle β of ATAN2 block 110 to a coordinate system compatible with reference command block 116.

The output $\dot{\theta}_s$ of rate gyro 102 and output angle β of ATAN2 block 110 is coupled to inputs of filter 112. In one embodiment, filter 112 is implemented as a low pass filter in the computer system or microcontroller with local electronic memory according to equation (1):

$$\theta_T = A_1 * (\theta_{PREV} + \dot{\theta}_s * \Delta t) + (1 - A_1) * \beta \qquad (1)$$

where: $\theta_T$ is tibia angle
$A_1$ is a calibration coefficient
$\theta_{PREV}$ is previous $\theta_T$
$\Delta t$ is rate of time change Filter 112 operates to remove sensor noise and combines the calibration coefficient $A_1$ weighted output $\dot{\theta}_s$ of rate gyro 102, $\theta_{PREV}$, and angle β of ATAN2 block 110. The output of filter 112 is the tibia angle $\theta_T$. The calibration coefficient $A_1$ can be a value between zero and one, typically close to one. In one embodiment, calibration coefficient $A_1$ is 0.995. When tibia 68 is moving quickly, output $\dot{\theta}_s$ of rate gyro 102 dominates tibia angle $\theta_T$. When tibia 68 is moving slowly, output angle β of ATAN2 block 110 dominates tibia angle $\theta_T$ to reduce drift. Filter 112 corresponds to conditioning block 90 providing the conditioned state measurements in FIG. 5.

Tibia angle $\theta_T$ is input to the reference function in reference command block 116. Reference command block 116 is implemented in the computer system or microcontroller with local electronic memory and is represented as a continuous 3D control surface 118 in FIG. 7 relating ankle angle and nut position on the x,y axis to ankle moment on the z-axis. Control surface 118 is a continuous function of ankle angle $\theta_A$ and nut position $NP_0$ with corresponding ankle moments. Nut position generally refers to an amount of extension or absolute position of actuator 40. Nut position $NP_0$ is read from actuator 40 as the current vertical extension of the actuator. No extension of actuator 40 corresponds to zero nut position; maximum extension of the actuator is max nut position. In one embodiment, control surface 118 is determined by recording data from similar non-gait activities in an able-bodied individual.

Figure 7:
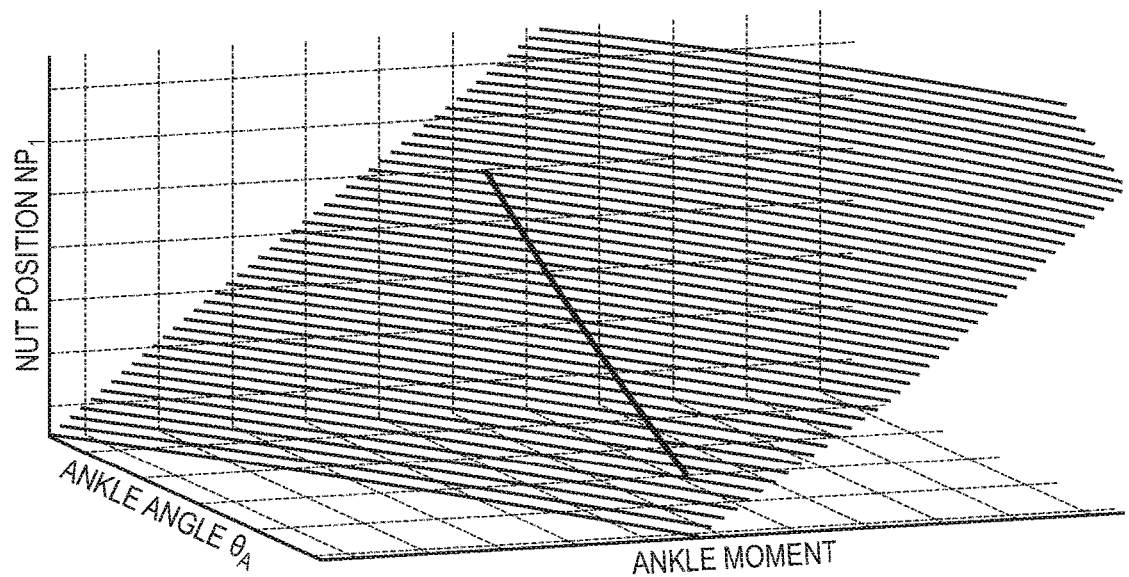
FIG. 7 illustrates a control surface of ankle angle and nut position with corresponding ankle moment.
Figure 8:
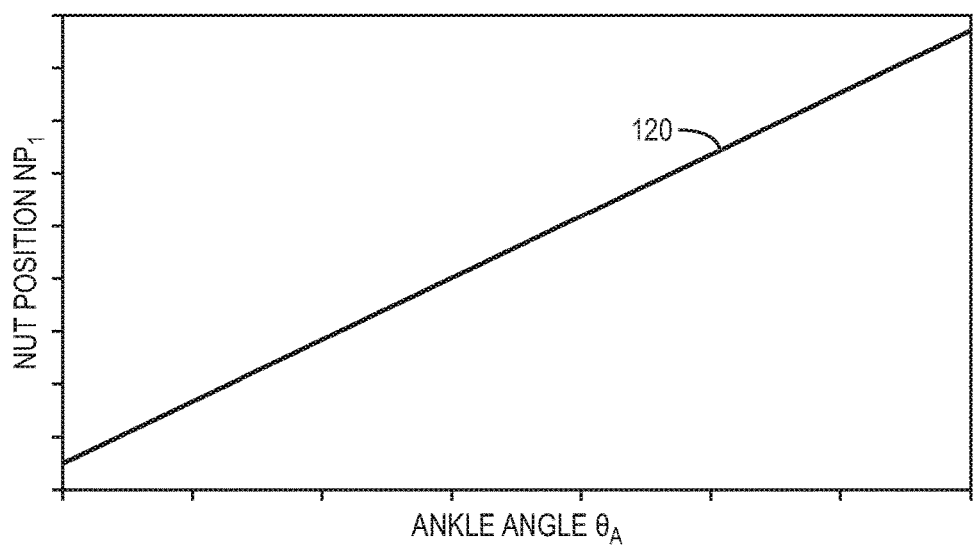
FIG. 8 illustrates a plot of ankle moment versus nut position for zero ankle moment.

For the scenario of user 10 seated in chair 70 in relaxed mode, ankle moment is zero and ankle angle $\theta_A$ for control surface 118 is made equal to tibia angle $\theta_T$. In particular, line 120 through control surface 118 in FIG. 7 represents relaxed mode of ankle prosthesis 14 with zero ankle moment, shown as a 2D graph in FIG. 8. For a given ankle angle $\theta_A$, line 120 shows the corresponding nut position $NP_1$ with zero ankle moment. Given tibia angle $\theta_T$ from filter 112 and present nut position $NP_0$ from actuator 40, with ankle angle $\theta_A$ made equal to tibia angle $\theta_T$, new nut position $NP_1$ is determined from line 120 of control surface 118 in reference command block 116.

Figure 9A:
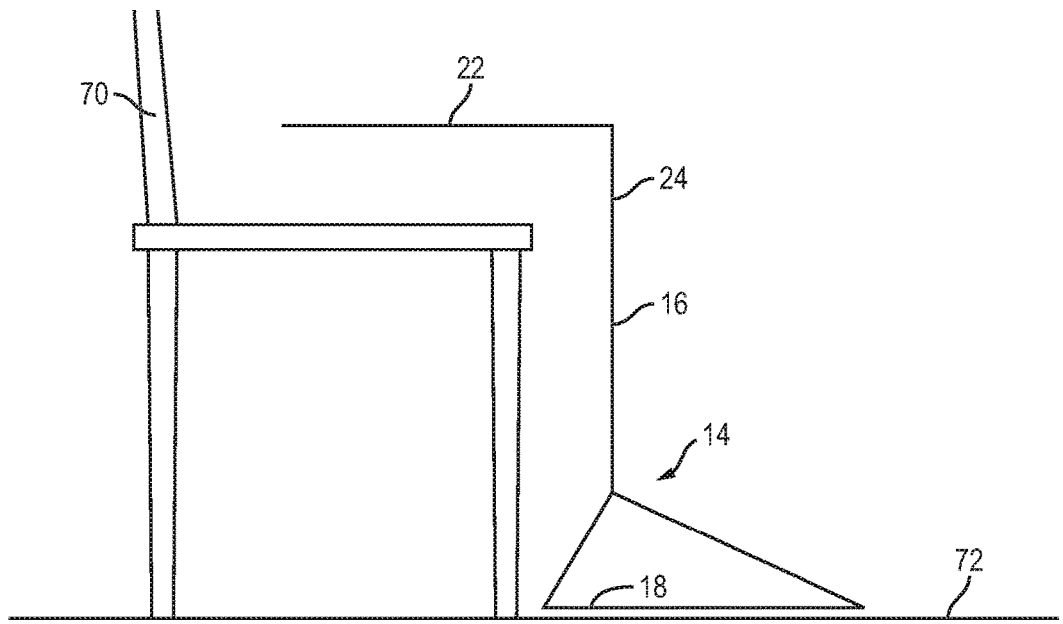
FIGS. 9a-9b illustrate a non-gait activity of shifting foot position while sitting.

Consider the non-gait motion of ankle prosthesis 14 from FIG. 4. User 10 is seated on chair or bench 70. Assume the left residual tibia 68 and ankle prosthesis 14 begin 90° with respect to the thigh of user 10, i.e. foot portion 18 flat on ground or floor 72 directly under the knee, see FIG. 9a. The position of ankle prosthesis 14 in FIG. 9a is zero ankle angle and zero ankle moment, also referred to as relaxed mode with no loading on ankle prosthesis 14. In relaxed mode, there is no loading or compression of the spring or extension of actuator 40 in ankle prosthesis 14. User 10 decides to move tibia 68 to position ankle prosthesis 14 under chair 70. The non-gait motion should a natural, biological motion, without an artificial or mechanical appearance. The muscles of user 10 act to move the left residual tibia 68, and accordingly ankle prosthesis 14, backward in a direction under chair 70 with an angular velocity $\dot{\theta}_s$ in sagittal direction 30.

For an able-bodied person, the natural, biological motion in moving the tibia from zero ankle angle to position the foot under chair 70 involves sliding the biological foot backward across floor 72. As the biological foot moves backward in the direction under chair 70, the heel naturally rises off floor 72, while the ball of the biological foot maintains contact with the floor.

Figure 9B:
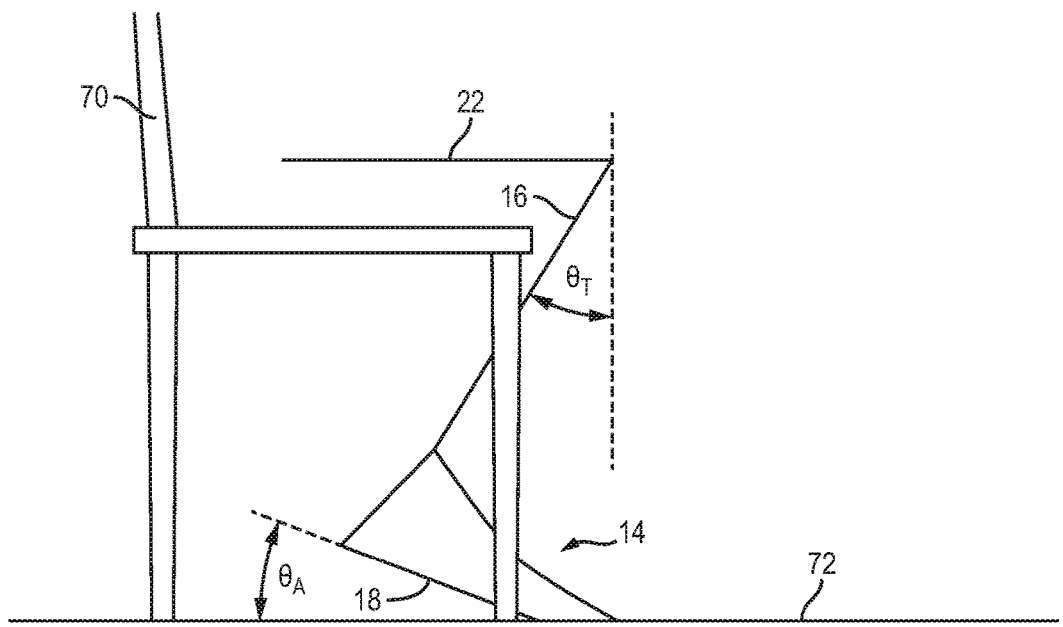

In a similar manner, rate gyro 102 measures angular velocity $\dot{\theta}_s$ of residual tibia 68 or ankle prosthesis 14 in sagittal direction 30. At the same time, accelerometer 102 measures acceleration Ẍ of residual tibia 68 or ankle prosthesis 14 in coronal direction 32, and accelerometer 104 measures acceleration Ÿ of residual tibia 68 or ankle prosthesis 14 in transverse direction 34 as an acceleration of residual tibia 68. Acceleration Ẍ and acceleration Ÿ are processed through ATAN2 block 110 to provide output angle β. Angular velocity $\dot{\theta}_s$ and angle β are processed through filter 112 to provide tibia angle $\theta_T$ during the slide of ankle prosthesis 14 across floor 72. The movement of the left residual tibia 68 to slide ankle prosthesis 14 under chair 70 increases tibia angle $\theta_T$. Given that present ankle angle $\theta_A$ is made equal to tibia angle $\theta_T$ for zero ankle moment, reference command block 116 converts the increasing ankle angle $\theta_A$ and present nut position $NP_0$ to new nut position $NP_1$, where $NP_1$ is greater than $NP_0$ due to the increasing tibia angle $\theta_T$ and ankle angle $\theta_A$ as per line 120 of control surface 118. Summation block 134 has inputs $NP_1$ and $NP_2$ and provides output $NP_3 = NP_1 + NP_2$ to control the extension of actuator 40 in ankle prosthesis 14. Nut position $NP_2$ is substantially zero while user 10 is seated in chair 70, i.e. no-load in relaxed mode with zero ankle moment. Nut position $NP_3$ is approximately equal to the new nut position $NP_1$ to extend the length of actuator 40. During the motion of positioning ankle prosthesis 14 under chair 70, the extension of actuator 40 in response to $NP_3 = NP_1 + NP_2$, where $NP_2 = 0$, causes the heel of foot portion 18 of ankle prosthesis 14 to rise off ground 72, while the ball of foot portion 18 remains in contact with the ground. As user 10 continues the slide of ankle prosthesis 14, tibia angle $\theta_T$ and corresponding ankle angle $\theta_A$ continue to increase and $NP_3$ continues to increase as well from line 120 of control surface 118, as shown in FIG. 9b. Accordingly, reference command block 116 maps increasing tibia angle $\theta_T$ to increasing nut position $NP_1$, and corresponding increasing $NP_3$ with $NP_2 = 0$, to control actuator 40 to lift the heel of foot portion 18 off ground 72, while the ball of foot portion 18 maintains contact with the ground. That is, reference command block 116 causes actuator 40 to dorsi flex ankle prosthesis 14 by same amount as the increasing tibia angle $\theta_T$ during the foot slide. The movement of ankle prosthesis 14 under chair 70, in response to control system 98, is a natural, biological motion involving a heel lift of foot portion 18 while the ball of foot portion 18 maintains contact with the ground, without an artificial or mechanical appearance.

Now consider the reverse non-gait motion of bringing ankle prosthesis 14 from the position of FIG. 9b to the position of 9a. User 10 decides to move tibia 68 to position ankle prosthesis 14 from a position under chair 70 to zero ankle angle, i.e. foot portion 18 flat on ground or floor 72 directly under the knee. Again, the non-gait motion should be a natural, biological motion, without an artificial or mechanical appearance. The muscles of user 10 act to move the left residual tibia 68, and accordingly ankle prosthesis 14, forward from under chair 70 with an angular velocity $\dot{\theta}_s$ in sagittal direction 30, opposite the previous example of sliding ankle prosthesis 14 backward under chair 70.

For an able-bodied person, the natural, biological motion in moving the tibia from a position of the foot under chair 70 to a position directly under the knee involves sliding the biological foot forward across floor 72. As the biological foot moves forward, the heel naturally returns to rest on floor 72.

In a similar manner, rate gyro 102 measures angular velocity $\dot{\theta}_s$ of residual tibia 68 or ankle prosthesis 14 in sagittal direction 30. At the same time, accelerometer 102 measures acceleration $\ddot{X}$ of residual tibia 68 or ankle prosthesis 14 in coronal direction 32, and accelerometer 104 measures acceleration $\ddot{Y}$ of residual tibia 68 or ankle prosthesis 14 in transverse direction 34 as an acceleration of residual tibia 68. Acceleration $\ddot{X}$ and acceleration $\ddot{Y}$ are processed through ATAN2 block 110 to provide output angle β. Angular velocity $\dot{\theta}_s$ and angle β are processed through filter 112 to provide tibia angle $\theta_T$ during the slide of ankle prosthesis 14 across floor 72. The movement of the left residual tibia 68 to slide ankle prosthesis 14 from under chair 70 decreases tibia angle $\theta_T$. Given that present ankle angle $\theta_A$ is made equal to tibia angle $\theta_T$ for zero ankle moment, reference command block 116 converts the decreasing ankle angle $\theta_A$ and present nut position $NP_0$ to new nut position $NP_1$, where $NP_1$ is less than $NP_0$ due to the decreasing tibia angle $\theta_T$ and ankle angle $\theta_A$ as per line 120 of control surface 118. Summation block 134 has inputs $NP_1$ and $NP_2$ and provides output $NP_3=NP_1+NP_2$ to control the extension of actuator 40 in ankle prosthesis 14. Nut position $NP_2$ is substantially zero while user 10 is seated in chair 70, i.e. no-load with zero ankle moment. Nut position $NP_3$ is approximately equal to the new nut position $NP_1$ to reduce the length of actuator 40. During the motion of positioning ankle prosthesis 14 to a position under the knee, the reduction in extension of actuator 40 in response to $NP_3=NP_1+NP_2$, where $NP_2=0$, causes the heel of foot portion 18 of ankle prosthesis 14 to return to ground 72. As user 10 continues the slide of ankle prosthesis 14, tibia angle $\theta_T$ and corresponding ankle angle $\theta_A$ continue to decrease and $NP_3$ continues to decrease as well from line 120 of control surface 118, as shown in FIG. 9a. Accordingly, reference command block 116 maps decreasing tibia angle $\theta_T$ to decreasing nut position $NP_1$, and corresponding decreasing $NP_3$ with $NP_2=0$, to control actuator 40 to lower the heel of foot portion 18 to ground 72. That is, reference command block 116 causes actuator 40 to relax ankle prosthesis 14 by same amount as the decreasing tibia angle $\theta_T$ during the forward foot slide. The movement of ankle prosthesis 14 from under chair 70 to zero ankle angle, in response to control system 98, is a natural, biological motion involving lowering a heel lift of foot portion 18 to the ground, without an artificial or mechanical appearance.

Now consider the scenario where user 10 decides to stand up from the seated position. Assume user 10 is sitting in chair 70, but has returned ankle prosthesis 14 to zero ankle angle, i.e. foot portion 18 is flat on ground or floor 72 directly under the knee as in FIG. 9a. The standing action imposes a load on ankle prosthesis 14. Returning to FIG. 6, ankle moment block 130 senses and measures moment from loading from the ankle angle and nut position, see FIG. 7. The output $M_A$ of ankle moment block 130 is routed to gain block 132. In one embodiment, gain block 132 is implemented in the computer system or microcontroller with local electronic memory according to equation (2):

$$NP_2 = A_2 \cos\left(\frac{M_A}{M_T} * \pi\right) - A_2 \quad (2)$$

where: $NP_2$ is nut position after gain 132
$A_2$ is a calibration coefficient
$M_T$ is maximum ankle moment The cos( ) function is unitless and calibration coefficient $A_2$ has units of length, e.g. centimeters or millimeters. The calibration coefficient $A_2$ corresponds to one-half the maximum extension of actuator 40. In one embodiment, calibration coefficient $A_2$ is value 10. When ankle prosthesis 14 is loaded, e.g. by standing from a seated position, gain 132 provides nut position $NP_2$ to summation block 134, i.e. $NP_3=NP_1+NP_2$. The output $NP_3$ of summation block 134 controls the extension of actuator 40 in ankle prosthesis 14. Nut position $NP_2$ is now a value greater than zero due to the loading on ankle prosthesis 14, while nut position $NP_1$ is substantially zero with zero ankle angle $\theta_A$. Accordingly, nut position $NP_2$ causes an extension of actuator 40, $NP_3=NP_1+NP_2$, where $NP_1=0$, to assist user 10 out of chair 70 upon loading of ankle prosthesis 14. The standing motion of user 10 from chair 70, in response to control system 98, is a natural, biological motion, without an artificial or mechanical appearance.

Control system 50 can be applied to other non-gait activity, such as shifting position of ankle prosthesis 14 while standing or leaning, as well as other random, complex, non-cyclic motions, such as dancing, exercise routines, sporting activities, random play with children, or other similar activities. Assume a non-gait sporting activity involving a forward motion, followed by a sudden stop and change of lateral direction. Sensing block 86 implements sensing kinematic states 82 and/or loading states 84 of mobile body 80 associated with the non-gait activity. Sensors 20 detect or measure one or more kinematic states 82, loading states 84, or combination of kinematic states 82 and loading states 84 of one or more mobile bodies 80 for the specific non-gait sporting activity. Conversion block 88 converts sensor data to a unit of measurement compatible with reference command block 94. Conditioning block 90 performs signal processing, to accentuate a relevant portion of the state measurements or provide sensor noise reduction. Transformation block 92 transforms the conditioned state measurements to be compatible with reference command block 94. For example, transformation block 92 transforms the time dependent conditioned state measurements to time independent transformed state measurements.

Reference command block 94 implements a control surface, similar to FIG. 7, that maps attributes of the non-gait activity to control of actuator 40. In the example of a sudden stop and change of lateral direction, the relevant attributes for the control surface may be lateral velocity and lateral position. The output of reference command block 94 controls ankle prosthesis 14 to respond in a natural, biological motion for the sudden stop and change of lateral direction, without an artificial or mechanical appearance. In the case of complex, multi-dimensional, non-gait activities, reference command block 94 may have a library of control surfaces each optimized to a particular phase of the overall activity. Control system 50 switches between the various implementations and control surfaces in response to sensor input for the particular phase of the overall non-gait activity.

While one or more embodiments of the present invention have been illustrated in detail, the skilled artisan will appreciate that modifications and adaptations to those embodi-

What is claimed:

1. A method of controlling a human assistance device, comprising:
   disposing a rate gyro, first accelerometer, and second accelerometer on a mobile body of the human assistance device for sensing a physical state of the mobile body to provide a physical state measurement;
   performing an ATAN2 function based on an output of the first accelerometer and an output of the second accelerometer;
   filtering electronically an output of the rate gyro and an output of the ATAN2 function using a controller of the human assistance device to provide a filtered physical state measurement, wherein the filtering is implemented according to $A_1*(\theta_{PREV}+\dot{\theta}_s*\Delta t)+(1-A_1)*\beta$, where A1 is a calibration coefficient, $\theta_{PREV}$ is a previous output of the filtering, $\Delta t$ is a rate of time change of $\dot{\theta}_s$, $\dot{\theta}_s$ is the output of the rate gyro, and $\beta$ is the output of the ATAN2 function;
   providing a reference function based on a non-gait activity; and
   applying the filtered physical state measurement to the reference function to generate a reference command using the controller to control a non-gait motion of the human assistance device.

2. The method of claim 1, wherein the reference command controls an actuator in the human assistance device.

3. The method of claim 2, further including applying a signal representative of a position of the actuator to the reference function to generate the reference command.

4. The method of claim 1, further including:
   measuring an ankle moment, wherein the human assistance device comprises an ankle prosthesis;
   applying a gain to the ankle moment; and
   summing the ankle moment after gain with an output of the reference function to generate the reference command.

5. The method of claim 4, wherein the gain is implemented as $A_2$ cos $$\left(\frac{M_A}{M_T}*\pi\right)-A_2,$$

where $A_2$ is a calibration coefficient, $M_A$ is the ankle moment, and $M_T$ is a maximum ankle moment.

6. A method of controlling a human assistance device, comprising:
   disposing a plurality of sensors on a mobile body of the human assistance device to measure a physical state of the mobile body and obtain a physical state measurement from the sensors;
   filtering electronically the physical state measurement from the sensors using a controller of the human assistance device to provide a filtered physical state measurement, wherein the filtering is implemented according to $A_1*(\theta_{PREV}+\dot{\theta}_s*\Delta t)+(1-A_1)*\beta$, where A1 is a calibration coefficient, $\theta_{PREV}$ is previous output of the filtering, $\Delta t$ is a rate of time change of $\dot{\theta}_s$, $\dot{\theta}_s$ is an output of a rate gyro on the mobile body, and $\beta$ is an output of an ATAN2 function;
   providing a reference function based on a non-gait activity; and
   applying the filtered physical state measurement to the reference function to generate a reference command using the controller to control a non-gait motion of the human assistance device.

7. The method of claim 6, wherein the sensors include the rate gyro, a first accelerometer, and a second accelerometer.

8. The method of claim 7, further including performing the ATAN2 function based on an output of the first accelerometer and an output of the second accelerometer, wherein filtering the physical state measurement includes filtering an output of the rate gyro and an output of the ATAN2 function.

9. The method of claim 6, wherein the reference command controls an actuator in the human assistance device, and a signal representative of a position of the actuator is applied to the reference function to generate the reference command.

10. The method of claim 6, further including:
    measuring an ankle moment, wherein the human assistance device comprises an ankle prosthesis;
    applying a gain to the ankle moment; and
    summing the ankle moment after gain with an output of the reference function to generate the reference command.

11. The method of claim 10, wherein the gain is implemented as $A_2$ cos $$\left(\frac{M_A}{M_T}*\pi\right)-A_2,$$

where $A_2$ is a calibration coefficient, $M_A$ is the ankle moment, and $M_T$ is a maximum ankle moment.

12. A method of controlling a human assistance device, comprising:
    sensing a physical state of a mobile body of the human assistance device by providing a physical state measurement of the physical state;
    filtering electronically the physical state measurement of the physical state of the mobile body using a controller of the human assistance device to provide a filtered physical state measurement, wherein the filtering is implemented according to $A_1*(\theta_{PREV}+\dot{\theta}_s*\Delta t)+(1-A_1)*\beta$, where A1 is a calibration coefficient, $\theta_{PREV}$ is a previous output of the filtering, $\Delta t$ is a rate of time change of $\dot{\theta}_s$, $\dot{\theta}_s$ is an output of a rate gyro on the mobile body, and $\beta$ is an output of an ATAN2 function;
    providing a reference function based on a non-gait activity; and
    applying the filtered physical state measurement to the reference function to generate a reference command using the controller to control a non-gait motion of the human assistance device.

13. The method of claim 12, further including disposing the rate gyro, a first accelerometer, and a second accelerometer on the mobile body for sensing the physical state of the mobile body.

14. The method of claim 13, further including performing an ATAN2 function based on an output of the first accelerometer and an output of the second accelerometer, wherein filtering the physical state measurement includes filtering an output of the rate gyro and an output of the ATAN2 function.

15. The method of claim 12, wherein the reference command controls an actuator in the human assistance device, and a signal representative of a position of the actuator is applied to the reference function to generate the reference command.

16. The method of claim 12, further including:
measuring an ankle moment, wherein the human assistance device comprises an ankle prosthesis;
applying a gain to the ankle moment; and
summing the ankle moment after gain with an output of the reference function to generate the reference command.

17. The method of claim 16, wherein the gain is implemented as $A_2 \cos$ $$\left(\frac{M_A}{M_T} * \pi\right) - A_2,$$

where $A_2$ is a calibration coefficient, $M_A$ is the ankle moment, and $M_T$ is a maximum ankle moment.

18. A human assistance device, comprising:
a prosthetic limb device;
a plurality of sensors coupled to the prosthetic limb device; and
a control system coupled to the prosthetic limb device, wherein the control system is configured to obtain a physical state measurement from the sensors and produce a reference command to control a non-gait activity of the prosthetic limb device and to apply an electronic filter that is implemented according to $A_1 *(\theta_{PREV} + \dot{\theta}_s * \Delta t) \pm (1-A_1)*\beta$, where A1 is a calibration coefficient, $\theta_{PREV}$ is a previous output of the filtering, $\Delta t$ is a rate of time change of $\dot{\theta}_s$, $\dot{\theta}_s$ is an output of a rate gyro on the mobile body, and $\beta$ is an output of an ATAN2 function.

19. The human assistance device of claim 18, wherein the sensors include the rate gyro, a first accelerometer, and a second accelerometer.

20. The human assistance device of claim 19, wherein the control system is configured to perform the ATAN2 function based on an output of the first accelerometer and an output of the second accelerometer; and wherein the electronic filter has a first input coupled to an output of the rate gyro, a second input coupled to the output of the ATAN2 function, and an output providing a filtered physical state measurement.

21. The human assistance device of claim 18, further including wherein the control system is configured to:
measure an ankle moment, wherein the prosthetic limb device comprises an ankle prosthesis;
apply a gain to the ankle moment; and
sum the ankle moment after gain with an output of the reference function to generate the reference command.

* * * * *

UNITED STATES PATENT AND TRADEMARK OFFICE
CERTIFICATE OF CORRECTION

PATENT NO. : 10,307,271 B2  
APPLICATION NO. : 15/341817  
DATED : June 4, 2019  
INVENTOR(S) : Matthew Aaron Holgate et al.

Page 1 of 1

It is certified that error appears in the above-identified patent and that said Letters Patent is hereby corrected as shown below:

In the Specification

In Column 6 at Line 40, change "$\theta_s$" to --$\dot{\theta}_s$--.

In Column 6 at Line 67, change "$\ddot{Y}$" to --$\ddot{X}$--.

In Column 7 at Line 4, change "$\theta_s$" to --$\dot{\theta}_s$--.

In the Claims

In Column 11 at approximately Line 20, in Claim 1, change "A1" to --$A_1$--.

In Column 11 at Line 61, in Claim 6, change "A1" to --$A_1$--.

In Column 12 at Line 43, in Claim 12, change "A1" to --$A_1$--.

In Column 14 at Line 2, in Claim 18, change "A1" to --$A_1$--.

Signed and Sealed this  
Twenty-sixth Day of November, 2019

Andrei Iancu  
*Director of the United States Patent and Trademark Office*